United States Patent
Lenfers et al.

(10) Patent No.: US 6,301,951 B1
(45) Date of Patent: Oct. 16, 2001

(54) METHOD OF CONTROLLING A SENSOR FOR DETERMINING AN OXYGEN CONCENTRATION IN A GAS MIXTURE

(75) Inventors: Martin Lenfers, Aidlingen; Lothar Diehl, Stuttgart; Jürgen Schwarz, Rutesheim, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/382,516

(22) Filed: Aug. 25, 1999

(30) Foreign Application Priority Data

Aug. 25, 1998 (DE) ................................. 198 38 466

(51) Int. Cl.[7] ...................... G01N 27/419; G01N 27/409
(52) U.S. Cl. ...................... 73/23.31; 204/424; 204/426
(58) Field of Search ............................. 73/23.31, 23.32; 204/406, 424, 425, 426, 427

(56) References Cited

U.S. PATENT DOCUMENTS

| 4,601,809 | * | 7/1986 | Kitahara | 204/406 |
| 4,718,999 | * | 1/1988 | Suzuki et al. | 204/406 |
| 4,803,866 | * | 2/1989 | Miki et al. | 73/23.32 |
| 5,672,811 | * | 9/1997 | Kato et al. | 73/31.05 |
| 5,686,654 | * | 11/1997 | Friese et al. | 73/23.32 |

* cited by examiner

Primary Examiner—Daniel S. Larkin
(74) Attorney, Agent, or Firm—Kenyon & Kenyon

(57) ABSTRACT

In a method of controlling a sensor for determining an oxygen concentration in a gas mixture, in particular in the exhaust gas of internal combustion engines, a detection voltage supplied by a Nernst measurement cell and corresponding to the oxygen concentration is transformed by a circuit arrangement into a pump voltage for a pump cell, and an anodic or cathodic limit current flows over the pump cell, depending on the oxygen content of the gas mixture. In stable operation of the sensor, during which an anodic limit current flows for a selectable period of time, the pump cell and/or the Nernst measurement cell receives at least one voltage pulse supplied independently by the measured detection voltage or the pump current thus established, so that the sensor is depolarized.

6 Claims, 1 Drawing Sheet

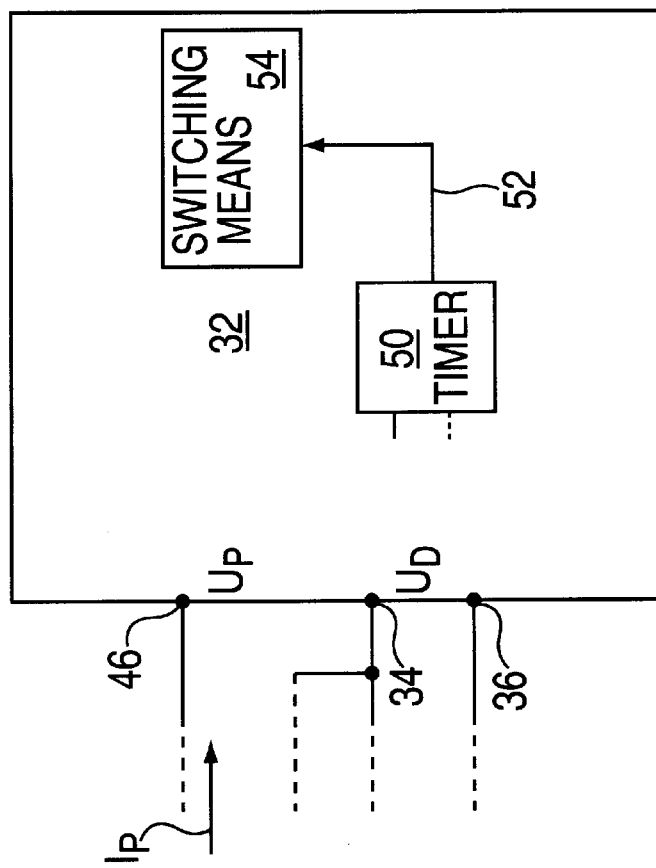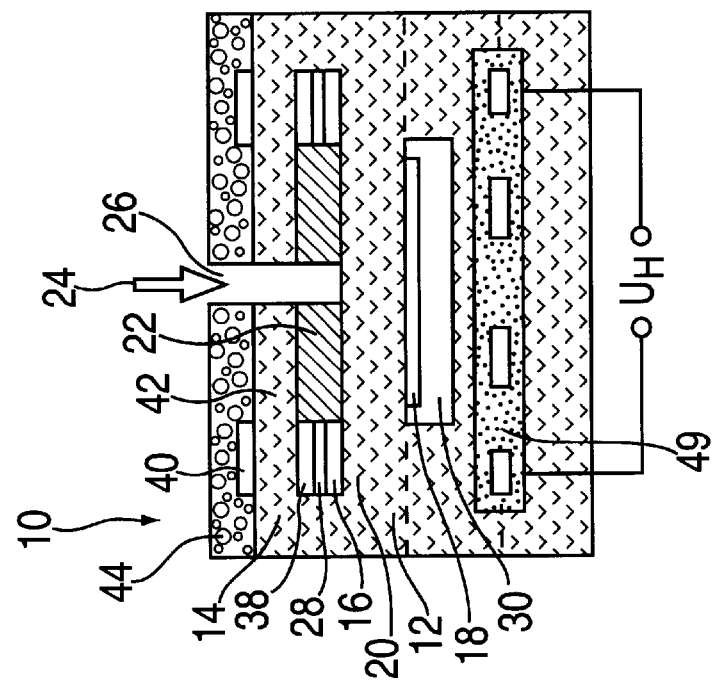

METHOD OF CONTROLLING A SENSOR FOR DETERMINING AN OXYGEN CONCENTRATION IN A GAS MIXTURE

FIELD OF THE INVENTION

The present invention relates to a method of controlling a sensor for determining an oxygen concentration in a gas mixture, in particular in the exhaust gas of internal combustion engines.

BACKGROUND INFORMATION

Sensors are used to determine the adjustment of a fuel-air mixture for operation of an internal combustion engine by determining the oxygen concentration in the exhaust gas of the internal combustion engine. The fuel-air mixture may be in the rich range, i.e., the fuel is present in stoichiometric excess, so that only a small quantity of oxygen is present in the exhaust gas in comparison with other partially unburned components. In the lean range, where there is more oxygen than air in the fuel-air mixture, the oxygen concentration in the exhaust gas is high accordingly.

Lambda probes are known for determining the oxygen concentration in the exhaust gas; these probes detect a lambda value of >1 in the lean range or <1 in the rich range, and a lambda value=1 in the stoichiometric range. In a known way, a Nernst measurement cell of the sensor supplies a detection voltage which is sent to a circuit arrangement. With the help of this circuit arrangement, the detection voltage is transformed to a pump voltage for a measurement probe (pump cell) which is also a part of the sensor. The measurement probe functions as a pump cell, where oxygen ions are pumped from a first electrode to a second electrode of the pump cell or vice versa, depending on the prevailing oxygen concentration in the gas mixture on which the measurement is to be performed. Depending on whether the lambda probe detects a rich range, i.e., a lambda value<1, or a lean range, i.e., a lambda value>1, the circuit arrangement determines whether an electrode of the pump cell connected to an active input of the circuit arrangement is switched as an anode or a cathode. The second electrode of the pump cell is connected to ground, so that either a cathodic limit current is set at the pump cell with a rich measurement gas or an anodic limit current is set with a lean measurement gas.

With a known sensor design, an electrode of the Nernst measurement cell and an electrode of the pump cell are each arranged in a joint cavity of the sensor, which is exposed to the exhaust gas through a diffusion barrier. If the fuel-air mixture to be monitored is in the lean range for a long period of time, oxygen ions diffuse out of the exhaust gas through the diffusion barrier into the joint cavity of the Nernst electrode of the Nernst measurement cell and the one pump electrode of the pump cell. According to the higher oxygen content in the lean range, an anodic limit current is applied to the pump cell by the circuit arrangement. In this way, additional oxygen ions are pumped into the joint cavity through the pump cell. One disadvantage of this is that if the internal combustion engine operates under lean conditions for a long period of time, e.g., several hours, fewer oxygen ions are pumped into the joint cavity of the Nernst electrode and the one pump electrode through the pump cell than would be necessary to maintain λ=1 in the cavity. This is due to falsification of the voltage of the Nernst measurement cell due to the participation of the Nernst electrode in the function of the internal pump electrode. This is the case when the internal pump electrode has become inactive due to long-lasting cathodic operation or due to manufacturing tolerance. However, due to the increasing concentration of oxygen ions in the joint cavity, the Nernst measurement cell determines that the fuel-air mixture is becoming richer, so that the sensor is subject to a rich drift leading to inaccuracies in the output signal.

SUMMARY OF THE INVENTION

The method according to the present invention for controlling a sensor offers the advantage that such a rich drift can be compensated. Due to the fact that the polarity of the pump voltage is reversed or the Nernst voltage is increased in selectable intervals after a selectable period of time during which sensor operation has been exclusively lean, it is advantageously possible to pump oxygen ions from the joint cavity of the Nernst electrode and the one pump electrode through the pump cell or the Nernst measurement cell, so that rich drift of a measurement probe can be compensated. Furthermore, CO coverage of the electrode can be eliminated. This activates the Nernst electrode, so that a difference in oxygen concentration between the Nernst electrode and a reference electrode again corresponds to the actual oxygen content in the gas mixture on which the measurement is to be performed. Brief evacuation of oxygen ions can be set according to the choice of the frequency and duration of pulses. The frequency and duration of pulses can be varied by an analysis and control circuit arrangement of the sensor as a function of an oxygen content detected in the gas mixture on which the measurement is to be performed. This ensures that only rich drift of the sensor will in fact be compensated, and reverse signal corruption due to a disturbance in adjustment of λ=1 in the cavity is prevented.

BRIEF DESCRIPTION OF THE DRAWING

The Figure shows a sectional diagram through a head of a sensor.

DETAILED DESCRIPTION

The Figure shows a sensor 10 in a sectional diagram through a measurement head. Sensor 10 is designed as a planar broad-band sensor having a number of individual layers arranged one above the other, optionally structured, for example, by film casting, punching, screen printing, lamination, cutting, sintering, or the like. Production of the layer structure will not be discussed further here as part of the present description because it is already known.

Sensor 10 is used to determine an oxygen concentration in the exhaust gases of internal combustion engines to obtain a control signal for adjusting a fuel-air mixture with which the internal combustion engine is operated. Sensor 10 has Nernst measurement cell 12 and a pump cell 14. Nernst measurement cell 12 has a first electrode 16 and a second electrode 18 between with there is a solid electrolyte 20. Electrode 16 is exposed to exhaust gas 24 to be measured through a diffusion barrier 22. Sensor 10 has a measurement orifice 26 which can receive exhaust gas 24. Diffusion barrier 22 extends at the base of measurement orifice 26, forming a cavity 28 withing which electrode 16 is arranged. Electrode 18 of Nernst measurement cell 12 is arranged in a reference air channel 30 and is exposed to a reference gas such as air which is applied to reference air channel 30. Solid electrolyte 20 is preferably made of zirconium oxide stabilized with yttrium oxide, while electrodes 16 and 18 are made of platinum, for example.

Sensor 10 is connected to a circuit arrangement 32, which is used to analyze signals of sensor 10 and to control the sensor. Electrodes 16 and 18 are connected to inputs 34 and 36 to which a detection voltage $U_D$ of Nernst measurement cell 12 is applied.

Pump cell 14 is composed of a first electrode 38 and a second electrode 40 between which is arranged a solid electrolyte 42. Solid electrolyte 42 is itself made of zirconium oxide stabilized with yttrium oxide, while again, electrodes 38 and 40 may be made of platinum. Electrode 38 is also arranged in cavity 28 and is thus also exposed to exhaust gas 24 through diffusion barrier 22. Electrode 40 is covered with a protective layer 44 which is porous so that electrode 40 is exposed directly to exhaust gas 24. Electrode 40 is connected to an input 46 of circuit arrangement 32, while electrode 38 is connected to electrode 16 and is jointly connected with it to input 34 of circuit arrangement 32.

Sensor 10 also includes a heating device 49 formed by a wave-form heater. Heating device 49 receives a heating voltage $U_H$.

Sensor 10 functions as follows:

Exhaust gas 24 is in cavity 28 above measurement orifice 26 and diffusion barrier 22 and is thus in contact with electrodes 16 of Nernst measurement cell 12 and electrode 38 of pump cell 14. Because of the oxygen concentration present in the exhaust gas on which the measurement is to be performed, an oxygen concentration difference is established between electrode 16 and electrode 18, which is exposed to the reference gas. Electrode 16 is connected by terminal 34 to a current source of circuit arrangement 32 which supplies a constant current. Because of an oxygen concentration difference prevailing at electrodes 16 and 18, a certain detection voltage $U_D$ is established. Nernst measurement cell 12 operates here as a lambda probe, which detects whether there is a high oxygen concentration in exhaust gas 24 or a low oxygen concentration. It is clear on the basis of the oxygen concentration whether the fuel-air mixture with which the internal combustion engine is operating is a lean or rich mixture. When there is a change from the rich range to the lean range or vice versa, detection voltage $U_D$ drops or increases accordingly.

With the help of circuit arrangement 32, detection voltage $U_D$ is used to determine a pump voltage $U_P$ which is to be sent to pump cell 14 between its electrodes 38 and 40. Pump voltage $U_P$ is negative or positive, depending on whether detection voltage $U_D$ signals that the fuel-air mixture is in the rich or lean range, so that electrode 40 is switched either as a cathode or as an anode. Accordingly, a pump current $I_P$ is established and can be measured by a measurement device of circuit arrangement 32. With the help of pump current $I_P$, oxygen ions are pumped either from electrode 40 to electrode 38 or vice versa. Measured pump current $I_P$ is used to control a device for adjusting the fuel-air mixture with which the internal combustion engine is operated.

In addition, it is assumed that the fuel-air mixture with which the internal combustion engine is operated is in a lean range for a long period of time. Therefore, a high oxygen content is established in exhaust gas 24 accordingly and is detected by sensor 10. A corresponding detection voltage $U_D$ is applied over the period of lean operation in accordance with the high oxygen content. Circuit arrangement 32 here includes a timer 50, with which detection voltage $U_D$ is sampled and a determination is made regarding the period of time over which this has been at a certain height. Timer 50 supplies a signal 52 when detection voltage $U_D$ is within a certain value range corresponding to lean operation of the internal combustion engine for a definable period of time, which may be, for example, several minutes, hours, or the like. During lean operation of the internal combustion engine, a cathodic pump current $I_P$ flows. Due to this cathodic pump current $I_P$, oxygen ions are pumped out of cavity 28 via electrode 38, so that over a long period of time fewer oxygen ions are pumped out of cavity 28 than enter cavity 28 from exhaust gas 24 through diffusion barrier 22 by cathodic pump current $I_P$. Due to the declining pump current of the pump cell, Nernst measurement cell 12 detects a fuel-air mixture which is becoming richer. Sensor 10 is thus subject to a rich drift. The reason for this is the faulty detection of the oxygen concentration in the cavity. The distribution of the pump current to the internal pump electrode and Nernst electrode 38, 16 changes over time to the detriment of the internal pump electrode, so detected Nernst voltage $U_D$ no longer corresponds to the concentration ratio between cavity 28 and reference air channel 30, but instead is falsified by a superimposed polarization voltage. It seems to be increased. Therefore, the system establishes a higher oxygen concentration than $\lambda=1$ in the cavity.

A switching means 54 which causes a pulse-like reversal of pump current $I_P$ is driven by signal 52 generated by timer 50. Thus, although pump current $I_P$ is flowing as an anodic current in accordance with the actual measurement of the oxygen concentration in exhaust gas 24, switching device 54 reverses it briefly to a cathodic pump current $I_P$ in a pulsed manner. This causes oxygen ions to be pumped from electrode 38 of pump cell 14 to electrode 40 and thus out of cavity 28 in accordance with this pulse-like reversal. A frequency and a duration of the pulses with which pump current $I_P$ is reversed briefly depends on signal 52, which in turn depends on detection voltage $U_D$. It is thus possible to supply different signals 52 at different oxygen concentrations in exhaust gas 24 and in a different time range within which detection voltage $U_D$ is in a certain value range. Thus, the frequency and/or pulse duration with which pump current $I_P$ is reversed can be made variable. The frequency and pulse duration are adjusted so that only the rich drift of sensor 10 is compensated.

According to another embodiment, in particular with a pumped reference, it is possible to provide for brief voltage pulses, which are above the measured Nernst voltage and have the same polarity, to be applied to Nernst measurement cell 12. According to detection voltage $U_D$ which is then impressed on the Nernst measurement cell, a great transport of oxygen ions out of cavity 28 into reference air channel 30 through electrode 16 is established. This also eliminates the polarization on electrodes 16 and 38 due to a declining oxygen ion content in cavity 28 during long-term lean operation. Due to the fact that oxygen ions in exhaust gas 24 cannot diffuse subsequently through diffusion barrier 22 as rapidly or cannot be pumped through pump cell 14 into cavity 28 as are pumped out through electrode 16, there is an activation of electrodes 16 and 38 which compensates for the rich drift. The pump status of the pump cell prevailing in lean operation supports this activation.

Thus, on the whole, the rich drift during long-term lean operation is eliminated by brief, defined rich operation of sensor 10.

What is claimed is:

1. A method of controlling a sensor for determining an oxygen concentration in a gas mixture, comprising the steps of:

transforming, by a circuit arrangement, a detection voltage supplied by a Nernst measurement cell and corresponding to an oxygen concentration into a pump voltage for a pump cell, one of an anodic limit current and a cathodic limit current flowing over the pump cell, depending on an oxygen content of the gas mixture; and in a stable operation of the sensor, during which the anodic limit current flows for a selectable period of time, supplying at least one voltage pulse independently by at least one of a measured detection voltage and an established pump current to at least one of the pump cell and the Nernst measurement cell, so that the sensor is depolarized.

2. The method according to claim 1, wherein the gas mixture is an exhaust gas of an internal combustion engine.

3. The method according to claim 1, wherein a polarity of the pump voltage is reversed in pulses, so that the cathodic limit current is established briefly.

4. A method of controlling a sensor for determining an oxygen concentration in a gas mixture, comprising the steps of:

transforming, by a circuit arrangement, a detection voltage supplied by a Nernst measurement cell and corresponding to an oxygen concentration into a pump voltage for a pump cell, one of an anodic limit current and a cathodic limit current flowing over the pump cell, depending on an oxygen content of the gas mixture;

in a stable operation of the sensor, during which the anodic limit current flows for a selectable period of time, supplying at least one voltage pulse independently by at least one of a measured detection voltage and an established pump current to at least one of the pump cell and the Nernst measurement cell, so that the sensor is depolarized; and applying a voltage higher than the detection voltage to the Nernst measurement cell in pulses.

5. A method of controlling a sensor for determining an oxygen concentration in a gas mixture, comprising the steps of:

transforming, by a circuit arrangement, a detection voltage supplied by a Nernst measurement cell and corresponding to an oxygen concentration into a pump voltage for a pump cell, one of an anodic limit current and a cathodic limit current flowing over the pump cell, depending on an oxygen content of the gas mixture;

in a stable operation of the sensor, during which the anodic limit current flows for a selectable period of time, supplying at least one voltage pulse independently by at least one of a measured detection voltage and an established pump current to at least one of the pump cell and the Nernst measurement cell, so that the sensor is depolarized; and determining at least one of a frequency and a duration of pulses, with which at least one of: (a) a polarity of the pump voltage is reversed and (b) the detection voltage is increased, by at least one of a duration and an intensity of a lean operation of the sensor.

6. A method of controlling a sensor for determining an oxygen concentration in a gas mixture, comprising the steps of:

transforming, by a circuit arrangement, a detection voltage supplied by a Nernst measurement cell and corresponding to an oxygen concentration into a pump voltage for a pump cell, one of an anodic limit current and a cathodic limit current flowing over the pump cell, depending on an oxygen content of the gas mixture;

in a stable operation of the sensor, during which the anodic limit current flows for a selectable period of time, supplying at least one voltage pulse independently by at least one of a measured detection voltage and an established pump current to at least one of the pump cell and the Nernst measurement cell, so that the sensor is depolarized; and determining at least one of a duration and an intensity of a lean operation of the sensor by monitoring at least one of the detection voltage, the Nernst measurement cell, and the pump current of the pump cell.

* * * * *